(12) United States Patent
VanMiddendorp et al.

(10) Patent No.: US 12,076,267 B2
(45) Date of Patent: *Sep. 3, 2024

(54) EXTERNAL URINE COLLECTION SYSTEM AND RELATED METHOD

(71) Applicant: Corewell Health Innovations, LLC, Grand Rapids, MI (US)

(72) Inventors: Eric Jon VanMiddendorp, Grand Rapids, MI (US); Taylor S. Sims, Grand Rapids, MI (US); Abby A. Merritt, Wyoming, MI (US); Phillip N. Keshavarzi, West Olive, MI (US); Matthew S. Dykstra, Wyoming, MI (US); Tyler D. Kramer, Holt, MI (US); Amanda E. Stark, Rockford, MI (US); Chelsea M. Edge, Spring Lake, MI (US); Brandon D. Johnson, Hastings, MI (US); Jill M. Morris, Livonia, MI (US); John Farris, Grand Rapids, MI (US); Andrew T. Heuerman, Clarkston, MI (US); Kevin T. Weaver, Grand Rapids, MI (US); Md Maruf Hossain, Allendale, MI (US)

(73) Assignees: Grand Valley State University, Allendale, MI (US); Corewell Health Innovations, LLC, Grand Rapids, MI (US)

( * ) Notice: Subject to any disclaimer, the term of this patent is extended or adjusted under 35 U.S.C. 154(b) by 678 days.

This patent is subject to a terminal disclaimer.

(21) Appl. No.: 17/028,358

(22) Filed: Sep. 22, 2020

(65) Prior Publication Data
US 2021/0000637 A1 Jan. 7, 2021

Related U.S. Application Data

(63) Continuation of application No. 15/468,928, filed on Mar. 24, 2017, now Pat. No. 10,806,623.
(Continued)

(51) Int. Cl.
*A61F 5/455* (2006.01)
*A61F 5/441* (2006.01)
(Continued)

(52) U.S. Cl.
CPC .............. *A61F 5/455* (2013.01); *A61F 5/441* (2013.01); *A61F 5/443* (2013.01); *A61M 1/80* (2021.05);
(Continued)

(58) Field of Classification Search
CPC .......... A61M 5/32; A61M 1/00; A61M 27/00; A61M 1/80; A61F 5/44; A61F 5/455;
(Continued)

(56) References Cited

U.S. PATENT DOCUMENTS 2,944,551 A * 7/1960 Breer ...................... A61F 5/455
4/144.1
3,194,238 A 7/1965 Breece
(Continued)

FOREIGN PATENT DOCUMENTS

EP 0348071 B1 8/1994
WO 2008063623 A2 5/2008

OTHER PUBLICATIONS http://www.hollister.com/~/media/files/pdfs%E2%80%93for%E2%80%93download/continence%E2%80%93care/care-tips-for-female-urinary-pouch-922092-812.pdf.
(Continued)

*Primary Examiner* — Guy K Townsend
(74) *Attorney, Agent, or Firm* — Price Heneveld LLP

(57) ABSTRACT

An external urine collection system for collecting urine excreted by a user through the user's external urethral orifice includes a urinary assembly having a sleeve and a cup that define a collection chamber. The sleeve can be attached to an area around the user's external urethral orifice by an adhesive. The cup can be coupled to the sleeve through a male connector and female connector that form a liquid tight seal between the sleeve and the cup. An outlet is defined by at
(Continued)

least one of the sleeve and the cup for draining urine excreted by the user into the urinary assembly.

20 Claims, 13 Drawing Sheets

Related U.S. Application Data

(60) Provisional application No. 62/314,460, filed on Mar. 29, 2016.

(51) Int. Cl.
*A61F 5/443* (2006.01)
*A61M 1/00* (2006.01)
*A61F 13/45* (2006.01)
*A61F 13/82* (2006.01)

(52) U.S. Cl.
CPC ....... *A61F 2013/4562* (2013.01); *A61F 13/82* (2013.01)

(58) Field of Classification Search
CPC .......... A61F 5/441; A61F 5/443; A61F 13/82; A61F 2013/4562; A61B 19/00
See application file for complete search history.

(56) References Cited

U.S. PATENT DOCUMENTS

| | | | |
|---|---|---|---|
| 3,349,768 A * | 10/1967 | Keane | A61F 5/455 604/347 |
| 3,374,790 A * | 3/1968 | Mayhorne | A61F 5/455 604/347 |
| 3,528,423 A | 9/1970 | Lee | |
| 3,583,388 A | 6/1971 | Hovick | |
| 3,995,329 A | 12/1976 | Williams | |
| 4,198,979 A * | 4/1980 | Cooney | A61F 5/455 604/329 |
| 4,202,058 A | 5/1980 | Anderson | |
| 4,233,978 A | 11/1980 | Hickey | |
| 4,421,511 A | 12/1983 | Steer et al. | |
| 4,457,314 A | 7/1984 | Knowles | |
| 4,484,917 A * | 11/1984 | Blackmon | A61F 5/455 604/327 |
| 4,496,355 A | 1/1985 | Beecher | |
| 4,563,183 A | 1/1986 | Lowrey | |
| 4,568,339 A * | 2/1986 | Steer | A61F 5/455 4/144.3 |
| 4,583,983 A | 4/1986 | Einhorn et al. | |
| 4,681,572 A | 7/1987 | Tokarz | |
| 4,759,753 A | 7/1988 | Mohiuddin | |
| 4,795,449 A * | 1/1989 | Schneider | A61F 5/441 604/326 |
| 4,813,943 A | 3/1989 | Smith | |
| 4,822,347 A | 4/1989 | MacDougall | |
| 4,846,819 A * | 7/1989 | Welch | A61F 5/455 604/336 |
| 4,889,532 A | 12/1989 | Metz et al. | |
| 4,889,533 A | 12/1989 | Beecher | |
| 4,936,838 A | 6/1990 | Cross | |
| 5,004,463 A | 4/1991 | Nigay | |
| 5,053,027 A | 10/1991 | Manfredi | |
| 5,091,998 A * | 3/1992 | Witzke | A61F 5/4556 141/333 |
| 5,263,947 A | 11/1993 | Kay | |
| 5,295,983 A | 3/1994 | Kubo | |
| 5,735,835 A | 4/1998 | Holland | |
| 5,873,610 A * | 2/1999 | Szabo | F16L 37/0987 285/308 |
| 5,911,222 A | 6/1999 | Strohl | |
| 5,957,904 A | 9/1999 | Holland | |
| 5,966,748 A | 10/1999 | Young et al. | |
| 6,151,721 A | 11/2000 | Whitfield | |
| 6,183,454 B1 | 2/2001 | Levine | |
| 6,428,521 B1 | 8/2002 | Droll | |
| 6,464,674 B1 * | 10/2002 | Palumbo | A61F 5/451 604/385.01 |
| 6,537,262 B2 | 3/2003 | Thompson | |
| 6,699,174 B1 * | 3/2004 | Bennett | A61F 5/455 604/326 |
| 6,716,181 B2 * | 4/2004 | Spencer | A61F 5/455 600/574 |
| 7,181,781 B1 * | 2/2007 | Trabold | A61F 5/455 4/144.1 |
| 10,806,623 B2 * | 10/2020 | VanMiddendorp | A61F 5/441 |
| 2009/0056003 A1 | 3/2009 | Ivie et al. | |
| 2010/0174255 A1 * | 7/2010 | Axelsson | A61F 5/448 604/338 |
| 2011/0054426 A1 * | 3/2011 | Stewart | A61F 5/4556 604/347 |
| 2014/0325746 A1 | 11/2014 | Block | |
| 2017/0281399 A1 * | 10/2017 | VanMiddendorp | A61F 5/455 |
| 2021/0000637 A1 * | 1/2021 | VanMiddendorp | A61F 5/455 |

OTHER PUBLICATIONS https://www.rei.com/product/407267/sani-fem-freshette-feminine-urinary-director.
https://go-girl.com/.
http://www.viscot.com/download/Millie%20Female%20Urinal%20Instruction%20%5b1%5d.pdf.

* cited by examiner

EXTERNAL URINE COLLECTION SYSTEM AND RELATED METHOD

CROSS-REFERENCE TO RELATED APPLICATIONS

This application is a continuation of U.S. application Ser. No. 15/468,928, filed Mar. 24, 2017, now U.S. Pat. No. 10,806,623, which claims the benefit of U.S. Provisional Patent Application No. 62/314,460, filed Mar. 29, 2016, both of which are incorporated herein by reference in their entirety.

FIELD OF THE INVENTION

The present embodiments generally relate to an external urinary assembly and urine collection system and related methods of assembly and use.

BACKGROUND OF THE INVENTION

Female hospital patients experiencing urinary incontinence are traditionally treated using indwelling catheters. Inserting the catheter can be an invasive and time consuming procedure, as it requires the use of sterile practices. Inserting the catheter can be particularly challenging with elderly patients and patients who are overweight. Indwelling catheters can increase a patient's chance of developing a urinary tract infection (UTI), which requires treatment. UTIs can be painful for the patient and treatment of the infection can sometimes delay discharging the patient from the hospital. In addition, when the UTI is caused by the hospital's indwelling catheter, the hospital is often responsible for payment of the treatment. Thus, UTIs can be costly for hospitals in addition to the discomfort and inconvenience experienced by the patient.

There are several alternatives to indwelling catheters that do not require a component to be inserted into the patient's urethra. For example, one type of alternative includes a container or funnel that is pressed against the user's body. However, this type of system is not designed for mobile patients and can be uncomfortable to maintain in place, particularly while sitting. These types of systems are also not discrete.

Another alternative includes a bag that has an opening that is adhesively attached to the user's body. While this bag design does allow for some patient mobility, it does not protect the skin from the excreted urine, which can lead to irritation of the skin. In addition, the bag can become bulky and uncomfortable as it is filled with urine.

While various efforts have been made, there remains an opportunity to provide additional systems and methods for collecting urine excreted by a female user using a device that does not require insertion of components into the urethra of the female user.

SUMMARY OF THE INVENTION

An external urine collection system for collecting urine excreted by a user through the user's external urethral orifice and method of assembly and use are provided.

In one embodiment, an external female urine collection system for urine excreted by a female user through the female user's external urethral orifice is provided. The system includes a sleeve having an interface surface defining a first open end. The interface surface can be configured to be secured via an adhesive to an external surface of the female user. The sleeve can surround an external urethral orifice of the female user, distal from the external urethral orifice. The sleeve can define a second open end, opposite the first open end.

In another embodiment, a cup can be removably joined with the sleeve about the second open end of the sleeve and includes a cup inlet and a collection chamber. An outlet can be formed in the sleeve and/or the cup. A liquid tight seal can be formed by a male connector that is removably joined with the female connector. The male connector can be disposed on the sleeve, adjacent the second open end, or the cup inlet while the female connector can be disposed on the other of the sleeve, adjacent the second open end, and the cup inlet. A collection container can be fluidly coupled with the outlet via a tube.

In yet another embodiment, the sleeve, cup, liquid tight seal, and collection chamber are configured such that urine excreted by the female user flows in a sealed, non-leaking manner through the first and second open ends of the sleeve to the collection chamber through the cup inlet and from the collection chamber to the collection container through the outlet.

In still another embodiment, the female connector can include a pair of opposing flanges that define a channel adapted to receive the male connector therein to form a liquid tight seal between the sleeve and the cup. At least one of the pair of opposing flanges can be resilient and configured to flex toward and away from the other of the pair of opposing flanges. The male connector can include at least one leg adapted to fit and be received within the channel. At least one of the pair of opposing flanges can be adapted to resiliently flex away from the other as the at least one leg is inserted into the channel and press against the at least one leg within the channel.

In a further embodiment, a rib can be disposed on at least one of the pair of opposing flanges and extend into the channel and the male connector can define a seal recess. The rib can be adapted to engage the seal recess when the male connector is coupled to the female connector.

In another embodiment, the adhesive includes at least one of a hydrogel, a silicone-based adhesive, and a polyethylene glycol (PEG) hydrogel adhesive. In another embodiment, the sleeve and/or the cup is made from a flexible polymeric material.

In yet another embodiment, the sleeve interface surface can include an interface flange. The interface flange can be contoured to define a curved surface corresponding to a curvature of the female user's body adjacent the external urethral orifice.

In another embodiment, the system can include an undergarment. The undergarment includes a first portion configured to extend at least partially between a female user's legs, the first portion including an opening configured to receive the cup. A second portion is configured to extend around a female user's torso to hold the undergarment in place. The undergarment can be configured to provide at least intermittent support to the sleeve and/or the cup to facilitate maintaining the sleeve in place adjacent the female user's external urethral orifice.

In another embodiment, a pump can be joined with the outlet through the tube. The pump can be configured to apply negative pressure to the collection chamber of the cup to facilitate draining urine collected within the collection chamber to the collection container through the outlet. The pump can be one of a manual pump, a vacuum pump, and a peristaltic pump.

In yet another embodiment, the sleeve and/or the cup can include a vent opening configured to vent the collection chamber.

In a further embodiment, a method of managing urine excreted by a female user through the female user's external urethral orifice is provided. The method can include attaching a sleeve around the female user's external urethral orifice using an adhesive. The sleeve defines a first open end disposed adjacent, but external to the female user's external urethral opening, and a second open end, opposite the first open end. A cup can be connected to the sleeve, adjacent the second open end. The cup includes an inlet configured to removably couple with the sleeve adjacent the second open end and a collection chamber. One of the sleeve and the cup includes an outlet in fluid communication with the collection chamber. A liquid tight seal is formed between the sleeve and the cup when a male connector disposed the sleeve or the cup inlet couples with a female connector disposed on the other of the sleeve and the cup inlet. A collection container can be coupled with the outlet through a tube. Urine excreted by the female user can be collected in the collection chamber of the cup and drained through the tube into the collection container.

In another embodiment, the method includes connecting the cup before or after attaching the sleeve around the female user's external urethral orifice. In another embodiment, after the attaching the sleeve and connecting the cup, the cup can be separated from the sleeve while the sleeve remains attached to the female user.

These and other features and advantages of the present invention will become apparent from the following description of the invention, when viewed in accordance with the accompanying drawings and appended claims.

Before the embodiments are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION

Figure 1:
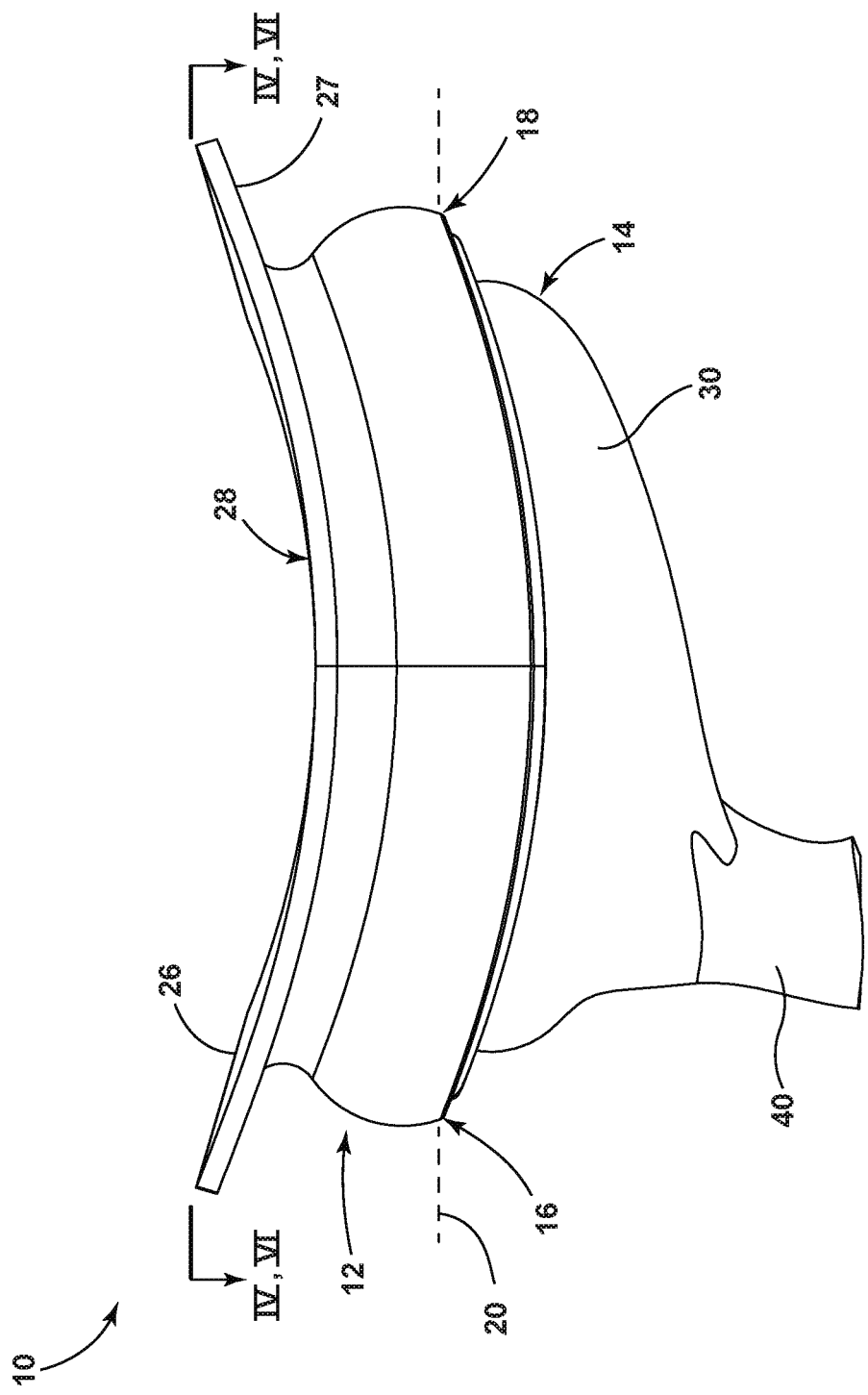
FIG. 1 is a side view of an external female urinary assembly according to an embodiment of the invention.
Figure 2:
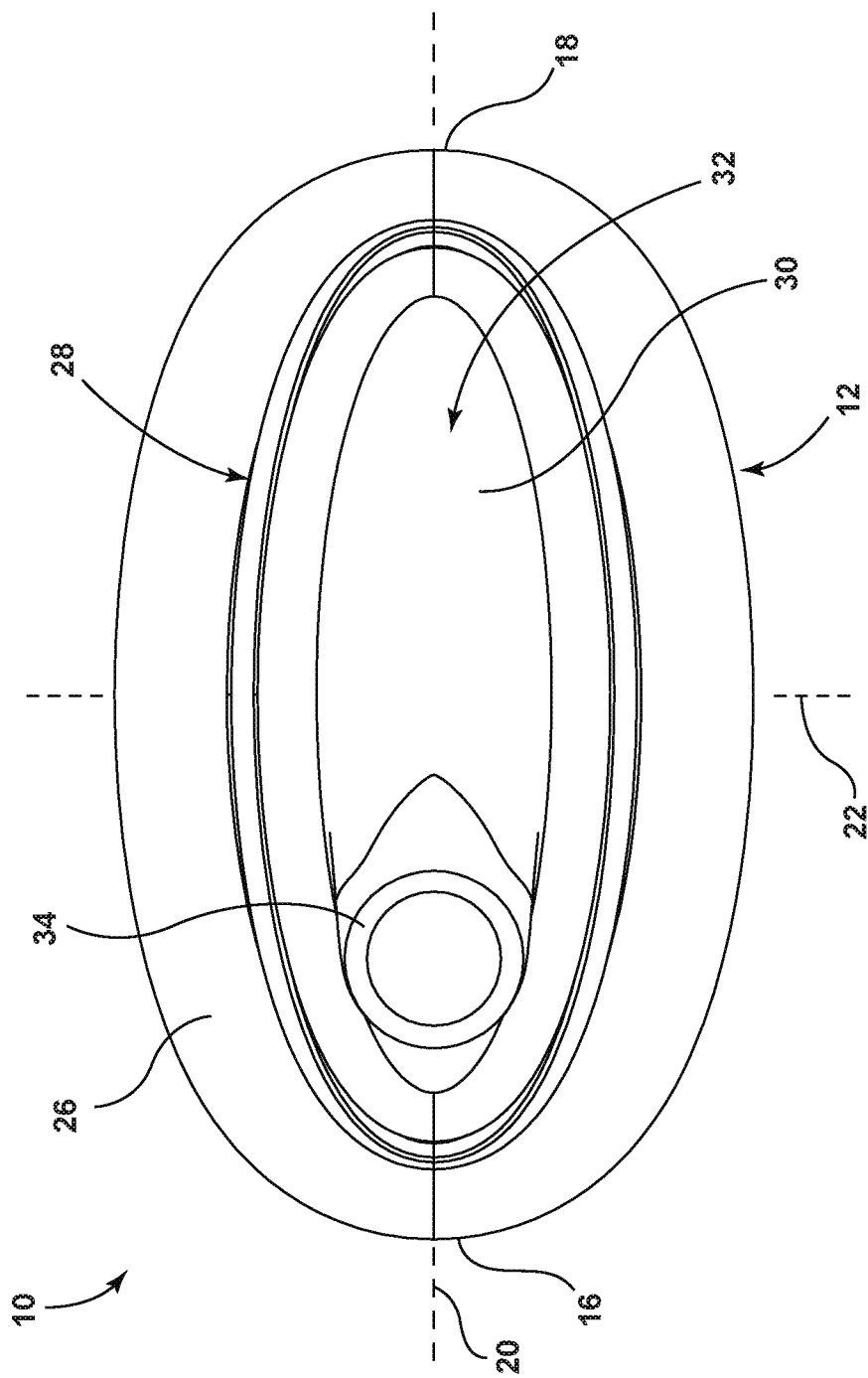
FIG. 2 is a top-down view of the external female urinary assembly of FIG. 1.
Figure 3:
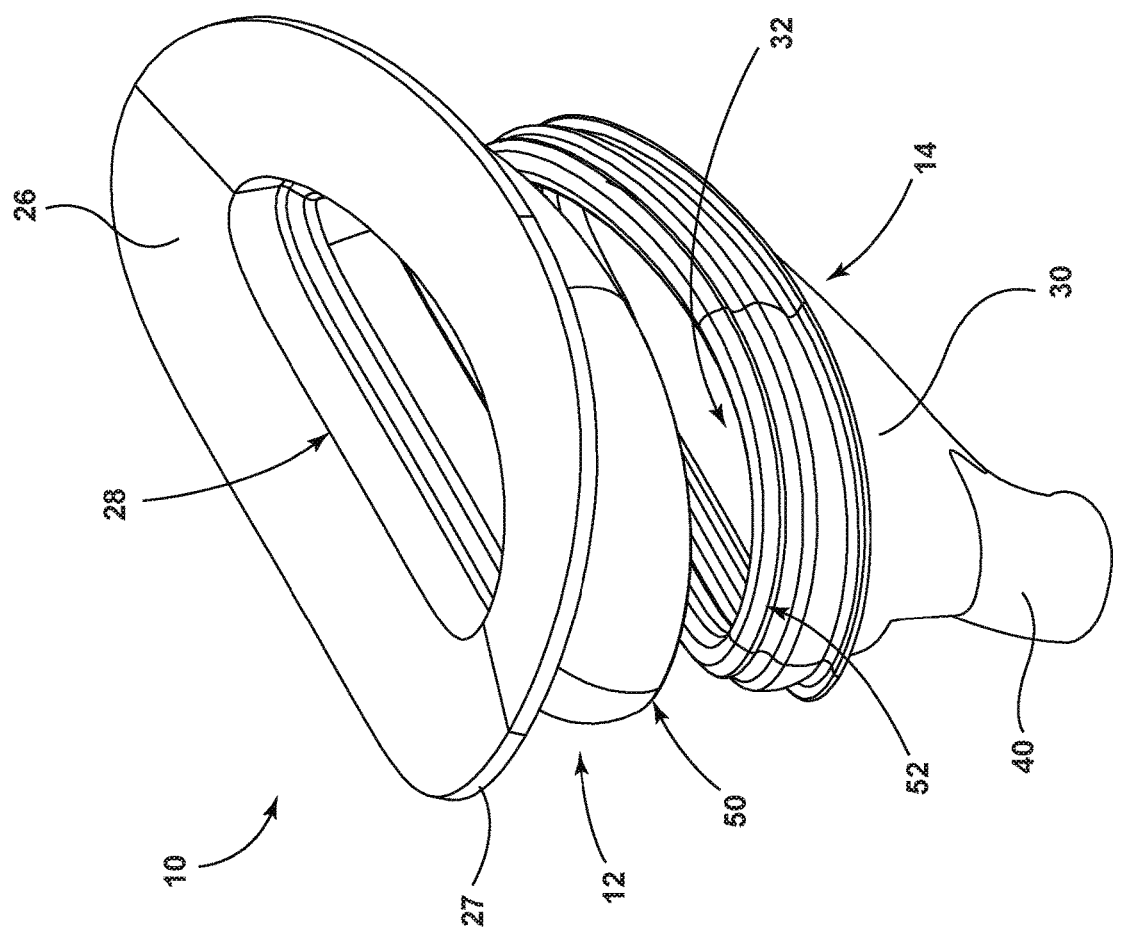
FIG. 3 is an exploded view of the external female urinary assembly of FIG. 1.

An external female urinary assembly is illustrated in FIGS. 1-3 and generally designated 10. The external female urinary assembly 10 is configured to be worn externally by a female user, around the user's urethral orifice, to collect urine excreted through the urethral orifice. As used herein, the term "external" when used to describe the urinary assembly 10 refers to an assembly which is adapted to be used without inserting components inside the female's urethra. The urinary assembly 10 is optionally part of a urine collection system, as will be described in further detail below, to collect and remove urine excreted from the female user. While the urinary assembly 10 is described in the context of collecting urine, it is to be understood that the urinary assembly 10 is not limited to collecting urine but may also collect other liquids excreted through the female user's urethral orifice in a similar manner.

Referring now to FIGS. 1-3, the urinary assembly 10 includes a sleeve 12 and a cup 14 that can be removably coupled and uncoupled to the sleeve 12. For the purpose of discussion, the urinary assembly 10 may be considered to include a posterior end 16 and an anterior end 18 according to the anatomical orientation of the urinary assembly 10 when worn by a user. When worn by a user, the posterior end 16 is positioned posterior of the user's urethral orifice while the anterior end 18 is positioned anterior of the user's urethral orifice. The urinary assembly 10 includes a longitudinal axis 20 extending between the posterior end 16 and the anterior end 18 and a lateral axis 22 extending perpendicular to the longitudinal axis 20.

Still referring to FIGS. 1-3, the sleeve 12 includes an interface surface 26 that is configured to be adhered to the user's body around the user's urethral orifice. The interface surface 26 generally defines a first sleeve open end or inlet 28 that is configured to allow urine excreted by the user to flow through the sleeve 12 and into the cup 14 when the urinary assembly 10 is worn by the user. The sleeve inlet 28 can be configured to surround the female user's external urethral orifice. Optionally, the sleeve inlet 28 is configured to surround the female user's labia majora.

The dimensions of the interface surface 26 can be selected to provide the desired amount of surface area for attaching the sleeve 12 to the user's body through an adhesive. For example, as illustrated in FIGS. 1 and 3, the interface surface 26 can be formed by a flange 27 extending outward and away from the sleeve inlet 28 that provides a surface area sufficient to form an adhesive bond with the user's skin to hold the urinary assembly 10 in place. Non-limiting examples of suitable adhesives include a hydrogel, a silicone-based adhesive, and a polyethylene glycol (PEG) hydrogel adhesive.

The cup 14 includes a wall 30 defining at least a portion of a collection chamber 32, together with the sleeve 12, in which urine excreted by the user can be collected during excretion and/or prior to removal. The collection chamber 32 is fluidly connected with an outlet 34 through which urine in the collection chamber 32 can drain from the collection chamber 32 and exit the urinary device 10 through a drain 40. The contours of the wall 30 forming the collection chamber 32 and/or the shape, location, and/or dimensions of the outlet 34 may be selected to provide the desired urine draining characteristics.

For example, the outlet 34 can be disposed in the wall 30 on the side of the lateral axis 22 adjacent the posterior end 16, as illustrated, to facilitate draining of the urine in the collection chamber 32. Optionally, the outlet 34 can be positioned anywhere along the longitudinal axis 20 between the anterior and posterior ends 16, 18. The wall 30 and outlet 34 can be symmetric about the longitudinal axis 20 and asymmetrical about the lateral axis 22, as illustrated. Optionally, the wall 30 and/or outlet 34 are symmetric or asymmetric about one or both of the longitudinal axis 20 and the lateral axis 22.

The drain 40 can be in the form of a connector for connecting a drain tube or form a drain tube for draining the liquid flowing through the outlet 34 away from the urinary assembly 10. The drain 40 can be configured to connect with a drain tube for disposal of the drained urine in a collection container (not shown). Optionally, when the drain 40 includes a drain tube, the drain 40 connects directly with the collection container.

With reference to FIG. 3, the sleeve 12 includes a female connector 50 that is adapted to be removably joined with a corresponding male connector 52 on the cup 14 for forming a liquid tight seal between the sleeve 12 and the cup 14 and securing the sleeve 12 and cup 14 together. Optionally, the female connector 50 is carried by the cup 14 and the male connector 52 is carried by the sleeve 12.

Figure 4:
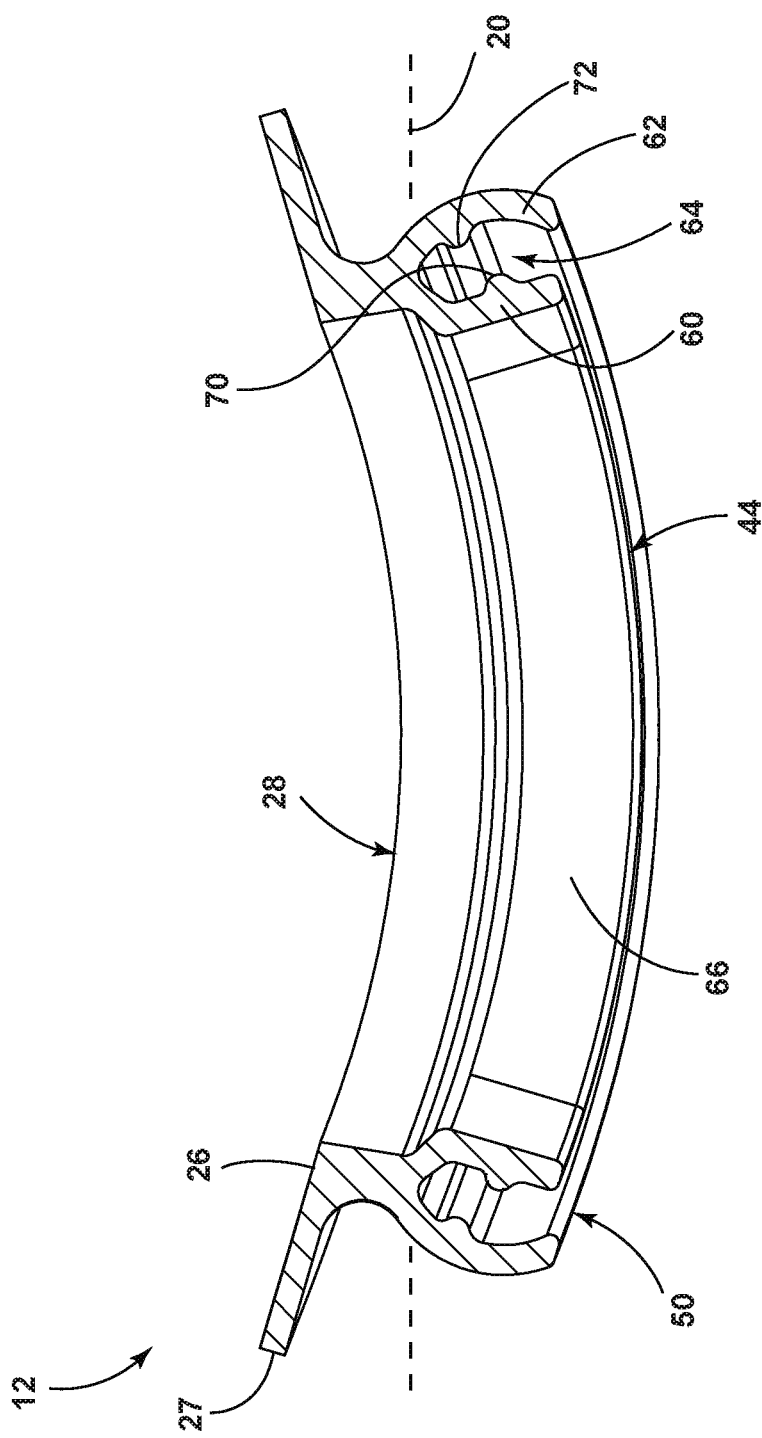
FIG. 4 is a cross-sectional view of a sleeve for use in an external female urinary assembly according to an embodiment of the invention.
Figure 5:
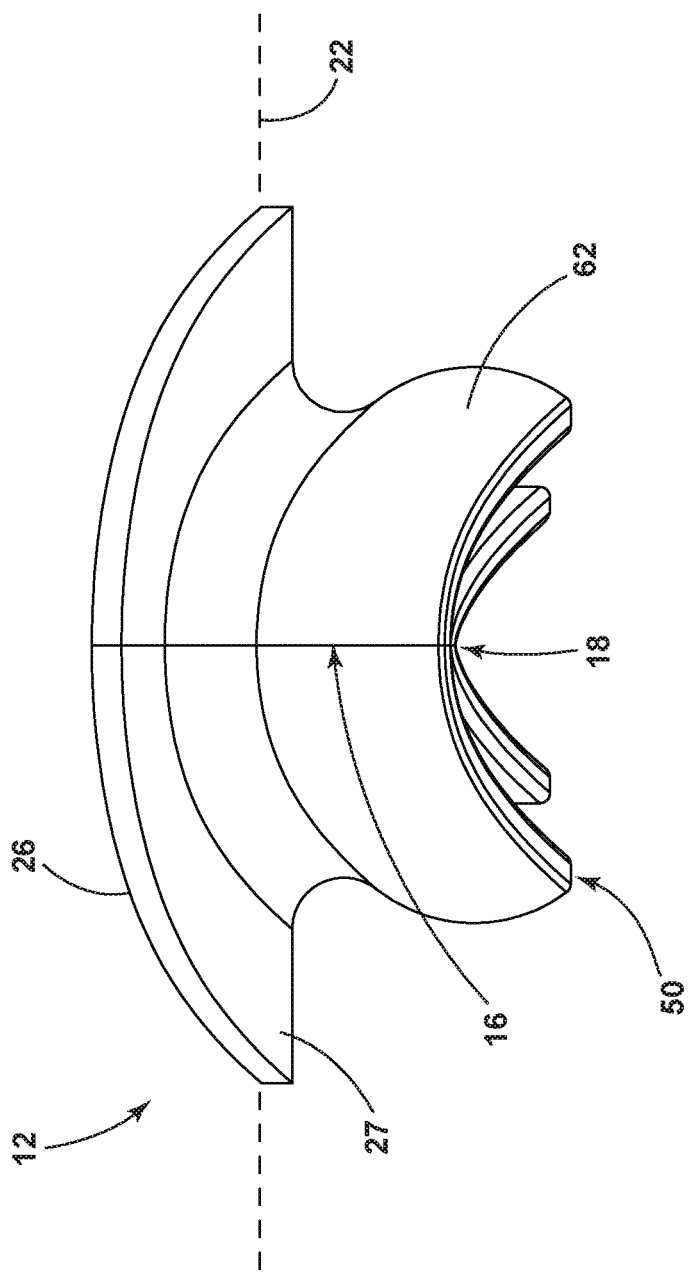
FIG. 5 is front view of the sleeve of FIG. 4.

With reference to FIGS. 4 and 5, the sleeve 12 includes a sleeve second open end or outlet 44, opposite the sleeve inlet 28, through which urine excreted by the user passes into the cup 14. The female connector 50 extends around the periphery of the sleeve outlet 44 and includes an inner flange 60 adjacent the collection chamber 32 and an opposing outer flange 62. The inner and outer flanges 60, 62 together define a channel 64 that is adapted to receive the male connector 52 therein for forming the liquid tight seal between the sleeve 12 and the cup 14.

As illustrated in FIG. 4, the inner flange 60 defines the sleeve outlet 44 and forms a sleeve wall 66 that, together with the cup wall 30, defines the collection chamber 32. Optionally, the sleeve wall 66 defining the sleeve outlet 44 and defining the collection chamber 32 is separate from the inner flange 60. In this optional configuration, the inner flange 60 forming the female connector 50 can extend around the periphery of the separate sleeve wall, thus forming a liquid tight seal around the periphery of the separate sleeve wall.

Still referring to FIG. 4, the inner and outer flanges 60 and 62 each include a rib 70 and 72, respectively, extending into the channel 64. The ribs 70, 72 can be configured to facilitate forming the liquid tight seal with the male connector 52. The ribs 70 and 72 can extend around the entire periphery of the channel 64 or only portions of the channel 64. Optionally, only one of the ribs 70 or 72 is disposed within the channel 64. Further optionally, one or both of the inner and outer flanges 60, 62 include multiple ribs 70, 72 to facilitate forming a liquid tight seal and securing the sleeve 12 and cup 14 together.

Referring now to FIGS. 4 and 5, the sleeve 12 can be contoured along one or both of the longitudinal and lateral axes 20, 22 to facilitate fitting and adhering the sleeve 12 to the user's body. The flange 27 forming the interface surface 26 can be contoured to define a surface that generally corresponds to the curvature of the female anatomy adjacent to the urethral orifice. The dimensions and contour of the sleeve 12 and/or the interface surface 26 can be varied to provide a sleeve 12 that is suitable for use by female user's having different body characteristics. For example, the dimensions and contour of the sleeve 12 and/or the interface surface 26 can be varied to accommodate users based on their height, weight, age, and/or body measurements. In one example, the sleeve 12 and/or interface surface 26 can be adapted to provide a sleeve 12 in multiple predetermined sizes, such as small, medium, large, and extra large, etc. to fit a range of physical body types.

The sleeve 12 can be made from a flexible material that facilitates conforming the interface surface 26 to the user's body in order to form a liquid tight seal between the user's body and the sleeve 12. Shaping the interface surface 26 to conform to the user's body also facilitates holding the urinary device 10 in place against the user's body during use. Forming the entire sleeve 12 from a flexible material can also increase the comfort of the user wearing the urinary device 10, particularly when the user is in motion or is sitting. Non-limiting examples of materials suitable for forming the sleeve 12 include silicone or a thermoplastic elastomer. Optionally, only the flange 27 is made from a flexible material.

Figure 6:
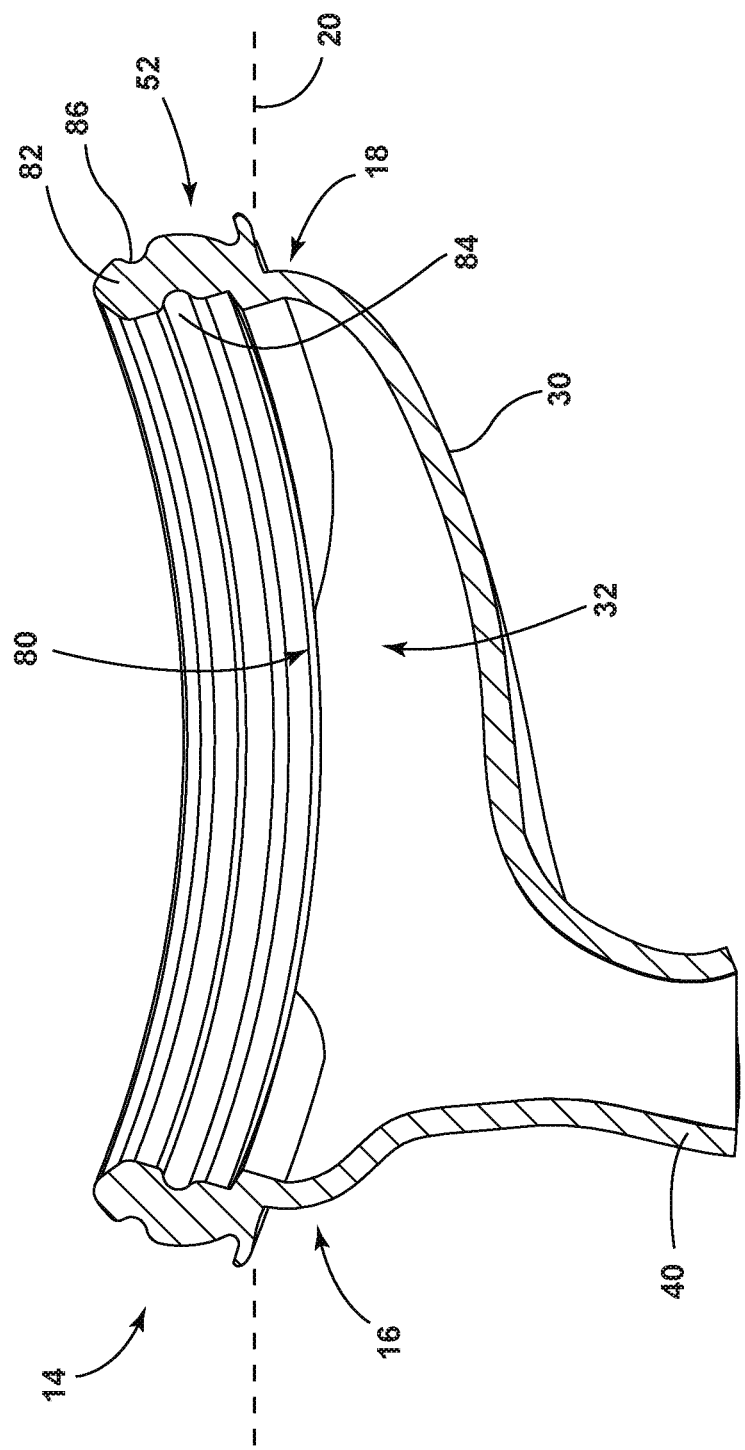
FIG. 6 is a cross-sectional view of a cup for use in an external female urinary assembly according to an embodiment of the invention.

Referring now to FIG. 6, the cup 14 includes a cup inlet 80 through which urine excreted into the sleeve 12 passes into the cup 14 for subsequent draining through the drain 40. The male connector 52 includes a leg 82 having an inner seal recess 84 on a side adjacent the collection chamber 32 and an outer seal recess 86 on the opposing side of the leg 82. The inner and outer seal recesses 84, 86 are configured to mate with the ribs 70, 72 on the inner and outer sleeve flanges 60 and 62, respectively, to form the liquid tight seal between the sleeve 12 and the cup 14. The inner and/or outer seal recesses 84, 86 can extend around an entire periphery of the cup inlet 80 or only a portion thereof. Optionally, the leg 82 includes a seal recess 84, 86 on a single side of the leg 82 corresponding to the location of a mating rib 70, 72 on one of the inner or outer sleeve flanges 60, 62. Further optionally, the leg 82 includes multiple seal recesses 84, 86 on one or both sides of the leg 82 based on the location of mating ribs 70, 72 on one or both of the sleeve flanges 60, 62.

In one embodiment, the location of the ribs 70, 72 and the seal recesses 84, 86 can be reversed. The ribs 70, 72 can be carried by the cup leg 82 and the mating seal recesses 84, 86 can be carried by the inner and outer sleeve flanges 60, 62 in order to form a liquid tight seal between the sleeve 12 and the cup 14.

The cup 14 is illustrated in FIG. 6 as having the leg 82 of the male connector 52 define the inlet 80 into the cup 14. Optionally, the inlet 80 into the cup 14 is defined by a wall that is separate from the male connector 52. In this optional configuration, the leg 82 extends around the wall defining the cup inlet 80 such that the male connector 52 can form a liquid tight seal with the female connector 50 around the periphery of the wall defining the cup inlet 80.

The cup 14 can be made from a material that is flexible to increase the comfort of the user wearing the urinary device 10, particularly when the user is in motion or is sitting. Non-limiting examples of materials suitable for forming the cup 14 include silicone or a thermoplastic elastomer. The cup 14 can be made from the same or different material than the sleeve 12.

Operation

Referring now to FIGS. 7-11, assembly and use of the urinary assembly 10 as part of an external female urine collection system is illustrated and described. The urinary assembly 10 is intended to be worn by a female user as an external catheter to collect and drain urine excreted by the female user away from the user's body. The urinary assembly 10 may be applied to the female user by the user herself or by another individual, such as a health care provider.

To fit the urinary assembly 10 onto the female user, the sleeve 12 is attached around the female user's external urethral orifice by an adhesive to form a liquid tight seal between the female user's body and the sleeve 12. The sleeve 12 can be separated from the cup 14 prior to attaching the sleeve 12 to facilitate aligning the sleeve 12 around the user's urethral orifice. When the cup 14 is separated from the sleeve 12, the female user's body can be viewed through the open sleeve inlet 28 and sleeve outlet 44 as the sleeve 12 is being fitted to the user. Optionally, the sleeve 12 can be attached to the female user's body with the cup 14 coupled to the sleeve 12.

The adhesive is adapted to form a bond between the user's body and the interface surface 26 of the sleeve 12 to hold the sleeve 12 in position against the user's body and to provide the liquid tight seal between the sleeve 12 and the user's body. The adhesive can be pre-applied to the interface surface 26 or applied to the interface surface 26 and/or the user's body at the time of attachment. In one example, the adhesive is pre-applied to the interface surface 26 and is covered with a release liner that is removed prior to attaching the sleeve 12 to the user's body.

The adhesive may be any adhesive that is suitable for use on human skin, is non-toxic, and is capable of providing a liquid tight seal and retaining the sleeve 12 in position on the female user's body for a predetermined period of time. The adhesive can be selected based on the ease in which the adhesive can be removed from the female user without excessive discomfort and/or pain to the female user. The adhesive can be configured to maintain the liquid tight seal and retain the sleeve 12 in place for a minimum period of time, such as 12 hours or 24 hours, for example.

One example of a suitable adhesive is a PEG hydrogel. Many types of PEG hydrogels are non-toxic, safe on sensitive skin, and can absorb enough moisture to form a liquid tight seal with the sleeve 12. Another example is a "smart" or environmentally-sensitive hydrogel that exhibits swelling and de-swelling behavior that is temperature sensitive. A temperature sensitive adhesive includes a lower critical solution temperature (LCST), above which the adhesive hydrogel de-swells and collapses. This type of temperature sensitive hydrogel can be removed by increasing the temperature of the adhesive to a temperature above the LCST. Yet another example of a suitable adhesive is a silicone gel adhesive, such as those conventionally used in wound care.

The formation of the liquid tight seal between the sleeve 12 and the female user's body is facilitated by the 3-dimensional contours of the sleeve 12 and/or the materials used to form the sleeve 12. The sleeve 12, including the interface surface 26 and/or the flange 27 can be configured to conform to the contours of the female user's body adjacent the external urethral orifice to facilitate forming the liquid tight seal between the sleeve 12 and the female user's body. Forming the sleeve 12 from a flexible material facilitates bending and/or flexing the sleeve 12 to provide a good fit of the sleeve 12 onto the female user. Optionally, the sleeve 12 can be provided in one of several sizes, such as small, medium, large, etc. to facilitate providing a good fit between the sleeve 12 and the female user's body. A sleeve 12 in the size which provides the best fit to the female user can be selected to facilitate forming the liquid tight seal around the female user's external urethral orifice.

Prior to attaching the sleeve 12 to the female user's body, the area around the external urethral orifice is optionally prepped to facilitate forming the liquid tight seal and forming a good attachment between the adhesive and the user's skin. Preparing the user's body can include cleaning the area around the external urethral orifice using water, soap, and/or alcohol and optionally drying the cleaned area. Preparing the area can also include shaving body hair in the area around the external urethral orifice to facilitate bonding between the user's skin and the adhesive attaching the sleeve 12.

Figure 7:
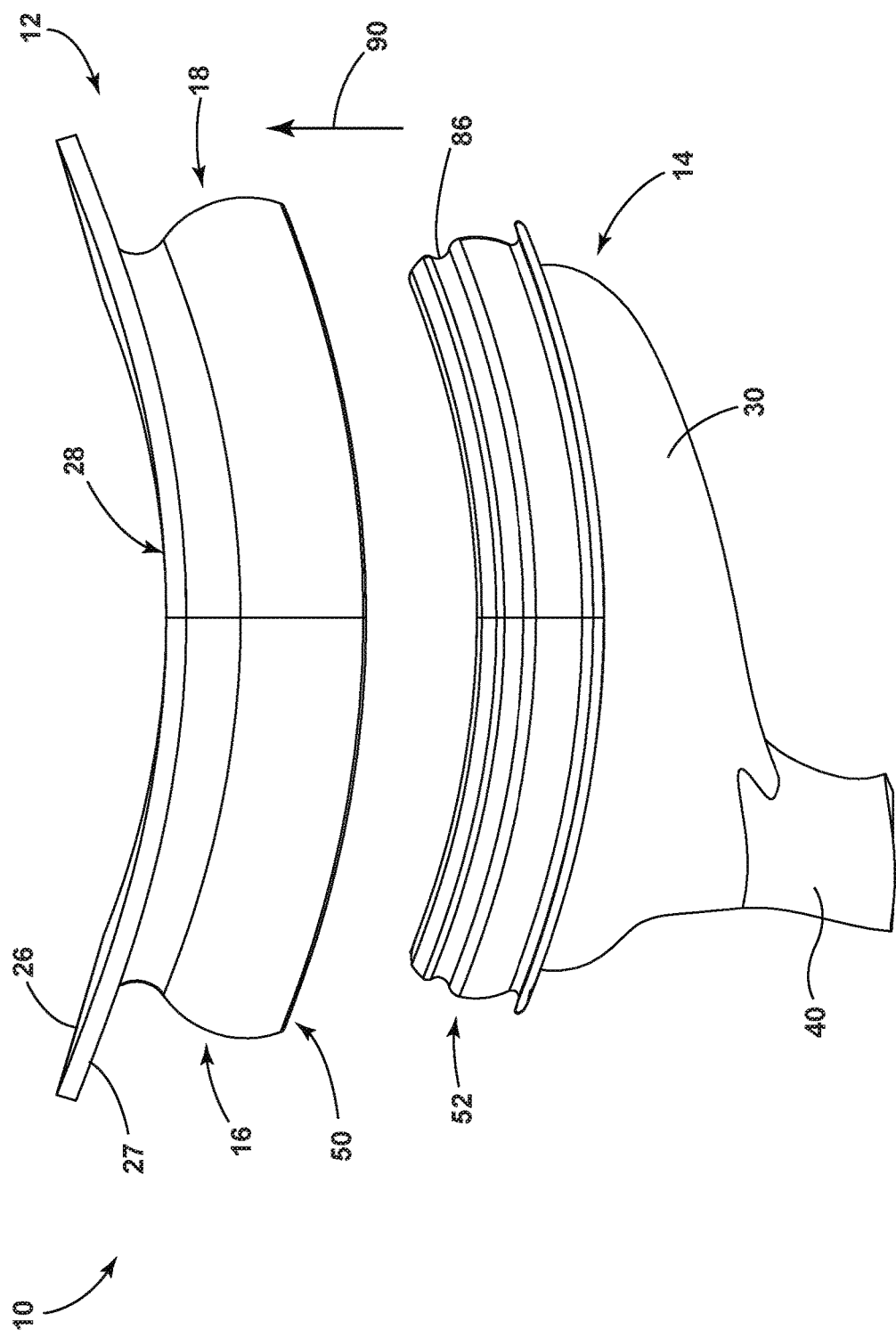
FIG. 7 is schematic illustration of a method of assembling an external female urinary assembly according to an embodiment of the invention.
Figure 8:
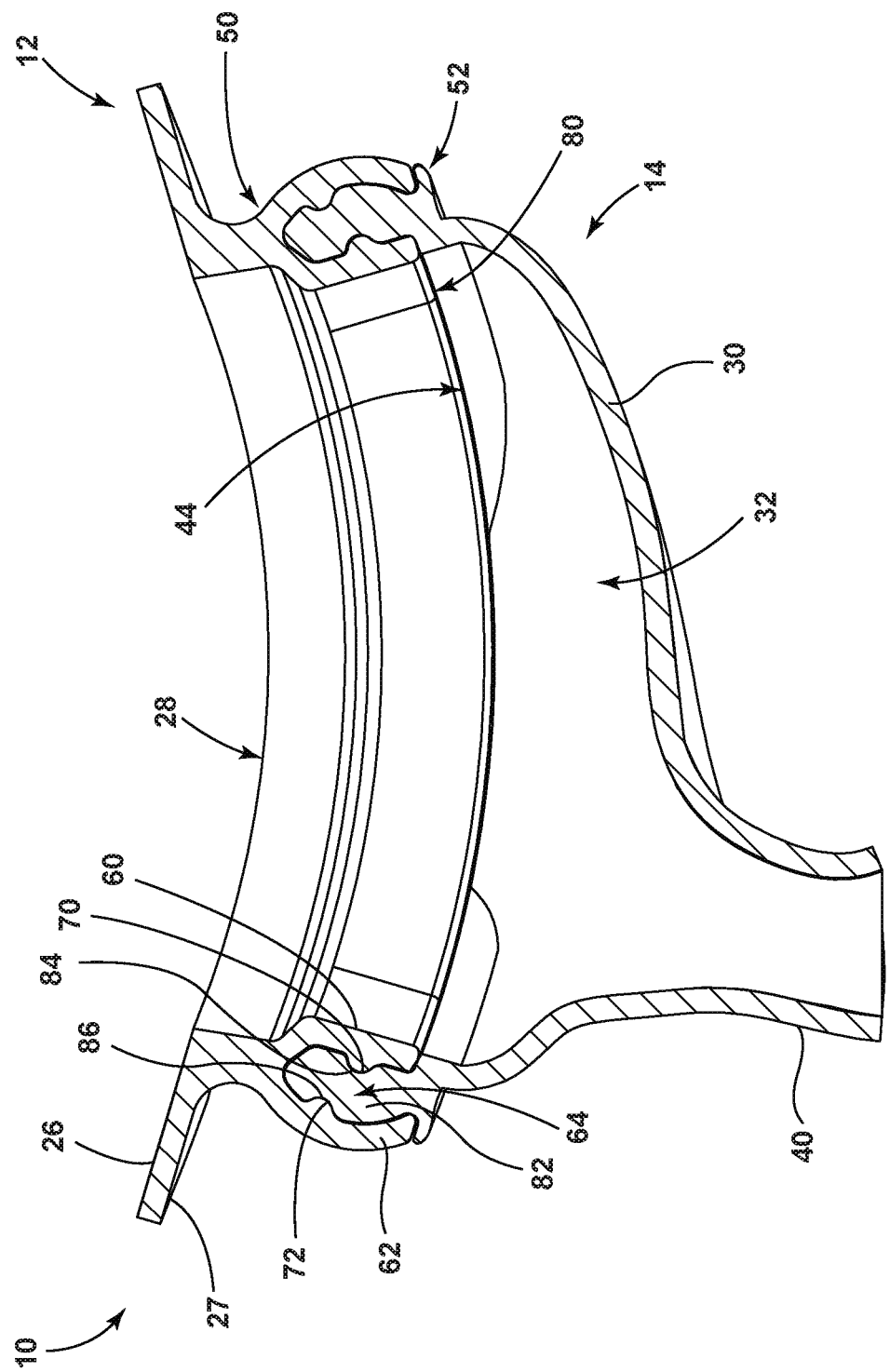
FIG. 8 is a cross-sectional view of a coupled sleeve and cup according to an embodiment of the invention.

Referring now to FIGS. 7-8, if the cup 14 is not already coupled to the sleeve 12, subsequent to attaching the sleeve 12 to the female user's body, the cup 14 can be fitted with the sleeve 12 to form a liquid tight seal between the sleeve 12 and the cup 14. To couple the sleeve 12 and the cup 14, the male connector 52 on the cup 14 is aligned with the female connector 50 on the sleeve 12 and the cup 14 is pressed against the sleeve 12, as illustrated by arrow 90. The female and male connectors 50, 52 are configured such that as the leg 82 of the male connector 52 is inserted into the channel 64 of the female connector 50, the inner and outer flanges 60 and 62 resiliently flex away from one another to receive the leg 82. Optionally, the female connector 50 can be configured such that only one of the inner or outer flanges 60, 62 is resilient and flexes away from the other flange when the leg 82 is inserted into the channel 64.

As the leg 82 is inserted into the channel 64, the leg 82 moves past the ribs 70, 72 in the inner and outer flanges 60, 62 until the ribs 70, 72 are received within the inner and outer seal recesses 84, 86. The ribs 70, 72 are adapted to engage the seal recesses 84, 86 to form a liquid tight seal between the female and male connectors 50, 52. The combination of a rib and sealing recess on both sides of the leg 82 provides a dual profile seal which facilitates forming a liquid tight seal between the sleeve 12 and the cup 14. Optionally, leg 82 can have dimensions that are slightly larger than the dimensions of the channel 64 when the inner and outer flanges 60, 62 are in an unflexed position to form an interference fit between the leg 82 and the inner and outer flanges 60, 62, which can facilitate forming a liquid tight seal between the sleeve 12 and cup 14.

The formation of a liquid tight seal between the sleeve 12 and the female user's body and the formation of a liquid tight seal between the sleeve 12 and the cup 14 provides a pathway through which urine excreted by the female user can be collected in a sealed, non-leaking manner. The liquid tight seal between the sleeve 12 and the female user's body allows the excreted urine to enter the collection chamber 32 through the sleeve inlet 28 in a non-leaking manner. The liquid tight seal between the sleeve 12 and the cup 14 allows the excreted urine to enter the cup 14 through the sleeve outlet 44 and cup inlet 80 in a non-leaking manner. The liquid tight seals between the sleeve 12 and the female user's body and between the sleeve 12 and the cup 14 provides a pathway through which urine excreted by the female user enters the sleeve 12 and flows through the cup 14 to the outlet 34 and then exits the urinary assembly 10 through the drain 40 in a sealed, non-leaking manner.

Still referring to FIGS. 7-8, subsequent to the attachment of the urinary device 10 to the female user, the cup 14 can be removed without detaching the sleeve 12 to allow for visual inspection and/or cleaning of the area encompassed by the sleeve 12. The cup 14 can be removed by withdrawing the cup 14 and unseating the male connector 52 from the female connector 50. Once the cup 14 is removed, the area around the external urethral orifice encompassed by the urinary assembly 10 can be inspected and optionally cleaned without having to separate the adhesively bonded sleeve 12 from the female user's body. Leaving the bonded sleeve 12 in place allows the area to be inspected and/or cleaned quickly and easily without having to remove and reapply adhesives. In addition, leaving the adhesively bonded sleeve 12 in place also avoids discomfort to the user associated with removing an adhesive from the skin. The separated cup 14 can also be cleaned and optionally replaced prior to re-coupling the cup 14 with the sleeve 12. The cup 14 can be re-coupled with the sleeve 12 through the female and male connectors 50, 52 in the same manner as described above.

The adhesive, and thus the sleeve 12, can be configured to be removed from the female user's body within a predetermined period of time and optionally replaced with a new sleeve 12. Optionally, the removed sleeve 12 can be re-used by applying a fresh layer of adhesive to the interface surface 26. The sleeve 12 may be removed after a predetermined period of time in order to provide a fresh adhesive to facilitate maintaining a liquid tight seal between the female user's body and the urinary assembly 10. The manner in which the sleeve 12 is separated from the female user's body can be based on the type of adhesive used to attach the sleeve 12.

For example, a hydrogel adhesive can be removed by flushing the area with water, optionally heated water, to facilitate removing the sleeve 12 and the adhesive while minimizing discomfort to the female user. If a temperature sensitive adhesive is used, the area may be heated or cooled to facilitate removal of the sleeve 12 and adhesive. For example, heated liquid or air can be used to increase the temperature of the area above the LCST for the adhesive to facilitate removal. Generally, the adhesive is selected to balance the desire to form a liquid tight seal between the sleeve 12 and the user's body and the desire to provide an attachment that can be removed after a predetermined period of time without excessive pain and/or discomfort to the user.

Figure 9:
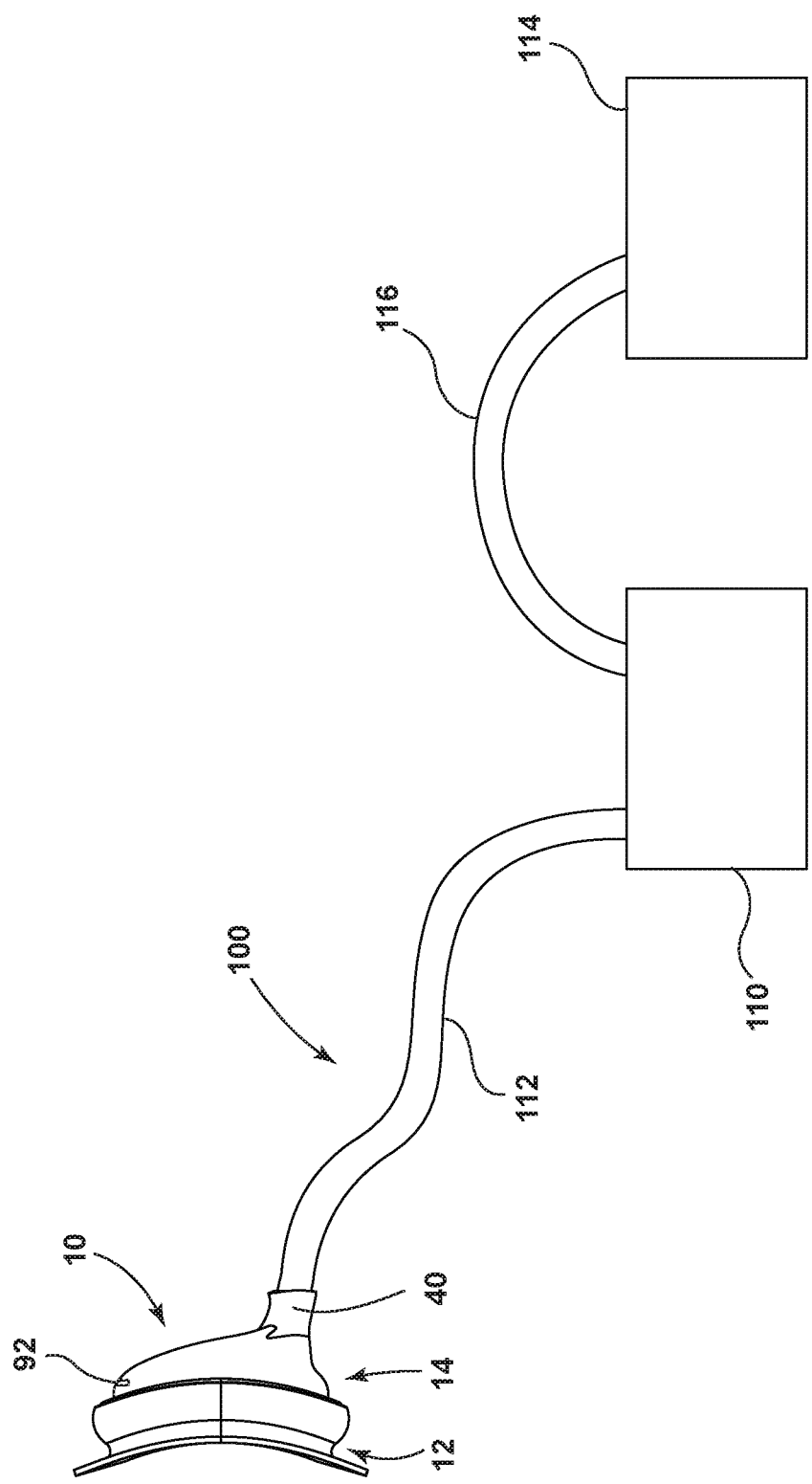
FIG. 9 is a schematic view of an external female urine collection system according to an embodiment of the invention.

Referring now to FIG. 9, the urinary assembly 10 can be coupled to a collection container 110 to as part of an external urine collection system 100 to collect the urine excreted by the female user for subsequent disposal. The urinary assembly 10 can be coupled to the collection container 110 prior to or subsequent to attaching the urinary assembly 10 to the female user's body. The urinary assembly 10 can be connected to the collection container 110 through a drain tube 112 that is coupled to the drain 40. Urine collected in the collection chamber 32 or the urinary assembly 10 can exit the collection chamber 32 through the outlet 34 and then flow through the drain tube 112 coupled to the drain 40 and into the collection container 110. The collection container 110 can be any suitable type of container, such as a leg bag or bedside bag, which is capable of storing urine until it can be disposed of. Optionally, the drain tube 112 and/or the collection container 110 includes a one-way seal to prevent urine from back-flowing into the urinary assembly 10.

The flow of urine from the urinary assembly 10 to the collection container 110 can be assisted by gravity. Optionally, the collection container 110 is coupled to a pump 114 by a tube 116. The pump 114 can apply negative pressure to the collection chamber 32 of the urinary assembly 10 to facilitate draining liquid from the cup 14 through the drain 40 and into the collection container 110. In one example, the pump 114 is a vacuum pump. The vacuum pump can be an individual unit or a part of an in-house suction system that can be coupled to the collection container. For patients who are mobile, gravity may be sufficient to drain urine from the urinary assembly 10 into the collection container 110 at a desired rate. However, for patients who are lying down and/or are not mobile, the pump 114 can be used to facilitate draining the urine from the urinary assembly 10 at a desired rate. In addition, the pump 114 can facilitate removing excess moisture that would otherwise remain within the urinary assembly 10.

The urinary assembly 10 optionally includes a vent 92 formed in either the sleeve 12 or the cup 14 for venting the collection chamber 32 to facilitate withdrawing urine from the urinary assembly 10. The vent 92 can also diminish the degree of suction felt on the female user's skin during evacuation of the urinary assembly 10, increasing the female user's comfort level.

Figure 10:
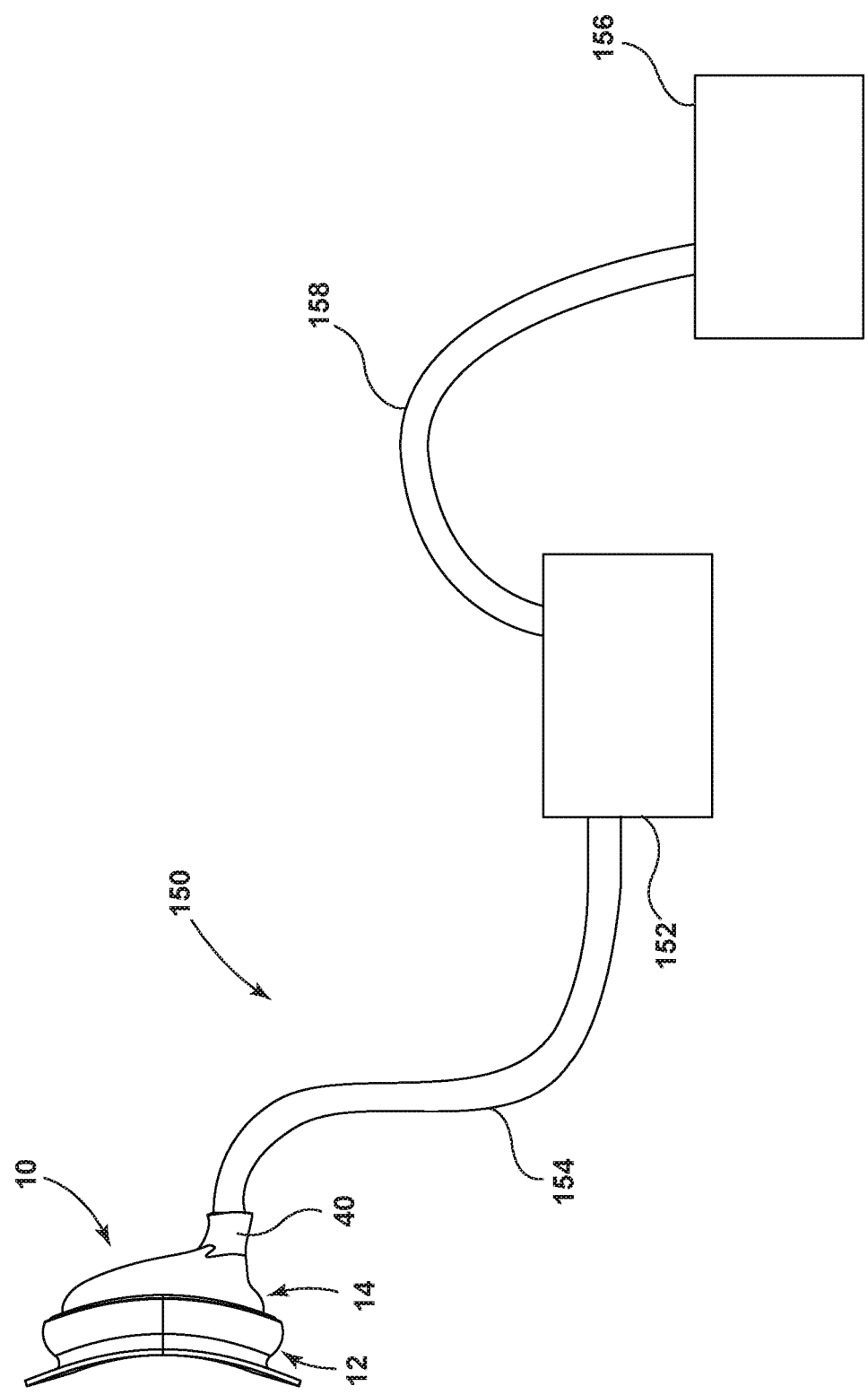
FIG. 10 is a schematic view of an external female urine collection system according to an embodiment of the invention.

Referring now to FIG. 10, another example of an external urine collection system 150 is illustrated. The system 150 is similar to the system 100 in structure, function, and operation, with several exceptions. For example, the manner in which negative pressure is applied to the collection chamber 32 differs. The system 150 includes a suction device 152 coupled to the urinary assembly 10 by a drain tube 154. The suction device 152 can be a manual or powered device capable of applying negative pressure to the collection chamber 32 to facilitate draining urine from the urinary assembly 10. The suction device 152 is coupled with a waste tube 158 for transporting the drained urine into a collection container 156 for storage and subsequent disposal. In one example, the suction device 152 can be a manual device, such as a squeeze pump or a bellows pump. In another example, the suction device 152 is a peristaltic pump.

Figure 12:
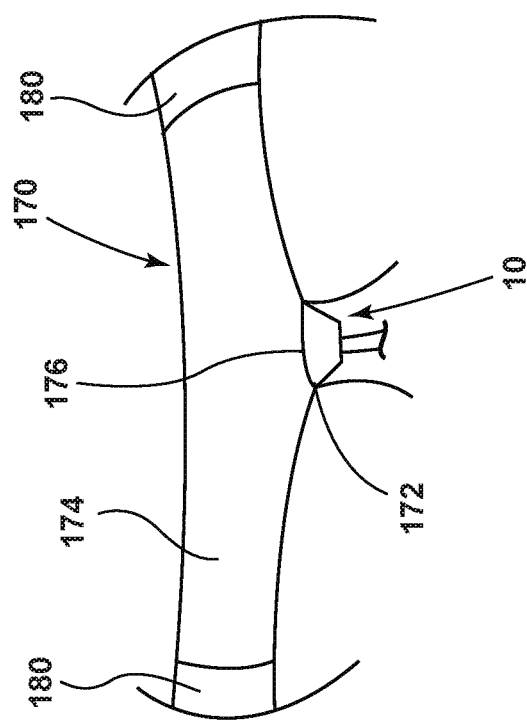
FIG. 12 is a front view of the undergarment of FIG. 11 as worn by a female user.
Figure 11:
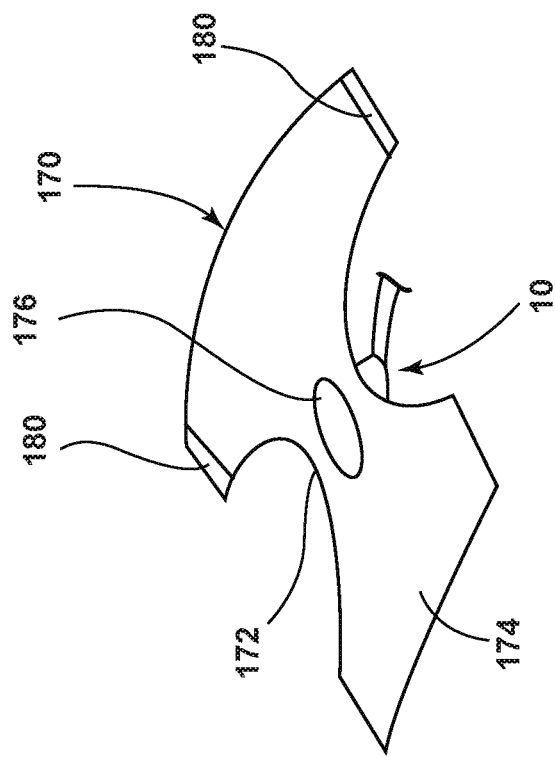
FIG. 11 is a perspective view of an undergarment for use with an external female urinary assembly according to an embodiment of the invention.

Referring now to FIGS. 11 and 12, an undergarment 170 configured to worn by the female user in combination with the urinary assembly 10 is illustrated. The undergarment 170 can be configured to provide at least intermittent support to the sleeve 12 and/or the cup 14 to facilitate retaining the urinary assembly 10 in a position adjacent the female user's body. The undergarment 170 can include a first portion 172 that is adapted to extend at least partially between the female user's legs when worn by the female user and a second portion 174 that is adapted to extend around the female user's torso and hold the undergarment 170 in place. The first portion 172 can include an opening 176 which is adapted to allow at least the drain 40 and/or the drain tube 112, 154 of FIGS. 9 and 10 to pass through.

Optionally, the opening 176 is configured such that the cup 14 passes through the opening 176 when the undergarment 170 is worn by the female user. In this configuration, the first portion 172 abuts the sleeve 12 to apply at least intermittent support to the sleeve 12 to help maintain the attachment between the user's body and the sleeve 12. This configuration may also allow the undergarment 170 to fit more comfortably on the user's body in a manner more similar to a traditional undergarment. Optionally, the opening 176 is defined by an elastic material such that the opening 176 can stretch to fit different size cups 14.

The undergarment 170 optionally includes fasteners 180 associated with the second portion 174 to facilitate dressing and removing the undergarment 170 from the female user's body. Non-limiting examples of suitable fasteners 180 includes buttons, snaps, hooks, and hook-and-loop tape. Optionally, the undergarment 170 does not include the fasteners 180 and is adapted to be pulled on and off the female user. The undergarment 170 can be provided in multiple sizes, such as small, medium, large, extra-large, etc. in a manner similar to traditional undergarments. Optionally, the dimensions of the opening 176 correspond to the size of the undergarment 170 such that larger undergarments 170 include larger openings 176 which are adapted to accommodate different sizes of urinary assemblies 10.

Figure 13:
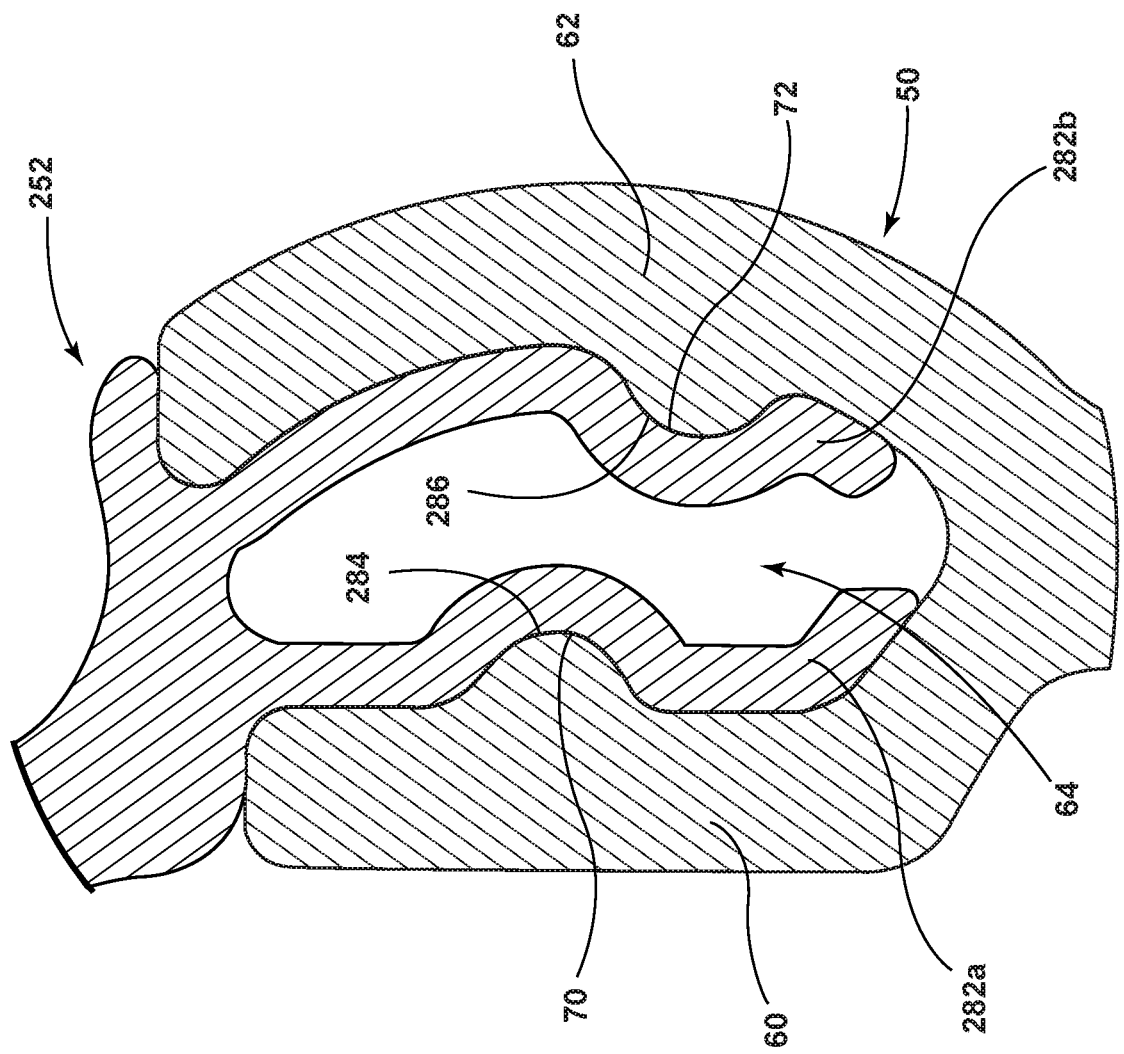
FIG. 13 is a cross-sectional view of a male and female connector for coupling a sleeve and a cup according to an embodiment of the invention.

Referring now to FIG. 13, an alternative embodiment of the male connector is shown and generally designated 252. This embodiment is similar in structure, function, and operation to the other embodiments described herein with several exceptions. For example, the male connector 252 includes multiple legs for forming the liquid tight seal, rather than a single leg. Therefore, elements of the male connector 252 similar to those of the male connector 52 are labeled with a prefix increased by 200.

The male connector 252 can be used with the female connector 50 to form a liquid tight seal between the sleeve 12 and the cup 14 in a manner similar to that described above with respect to FIGS. 7-8. The male connector 252 includes a pair of legs 282a, 282b which are adapted to be inserted into the channel 64 of the female connector 50. One or both of the legs 282a, 282b can be resiliently flexible such that the legs 282a, 282b flex inward, toward one another, as the male connector 252 is inserted into the channel 64 of the female connector 50. Optionally, the legs 282a, 282b do not flex during insertion into the channel 64, but rather one or both of the inner and outer flanges 60, 62 resiliently flex away from one another to receive the legs 282a, 282b. Further optionally, both the legs 282a, 282b and the inner and outer flanges 60, 62 have some degree of resilient flexibility to facilitate coupling of the male connector 252 with the female connector 50.

As the legs 282a, 282b are inserted into the channel 64, the legs 282a, 282b move past the ribs 70, 72 in the inner and outer flanges 60, 62 until the ribs 70, 72 are received within the inner and outer seal recesses 284, 286. The ribs 70, 72 are adapted to engage the seal recesses 284, 286 to form a liquid tight seal between the female and male connectors 50, 252. The combination of a rib and mating sealing recess formed with both legs 282a, 282b provides a dual profile seal which facilitates forming a liquid tight seal between the sleeve 12 and the cup 14. Optionally, legs 282a, 282b can have dimensions and/or be spaced such that the space defined by the legs 282a, 282b is slightly larger than the dimensions of the channel 64 when the inner and outer flanges 60, 62 are in an unflexed position to form an interference fit between the legs 282a, 282b and the inner and outer flanges 60, 62, which can facilitate forming a liquid tight seal between the sleeve 12 and cup 14.

Figure 14:
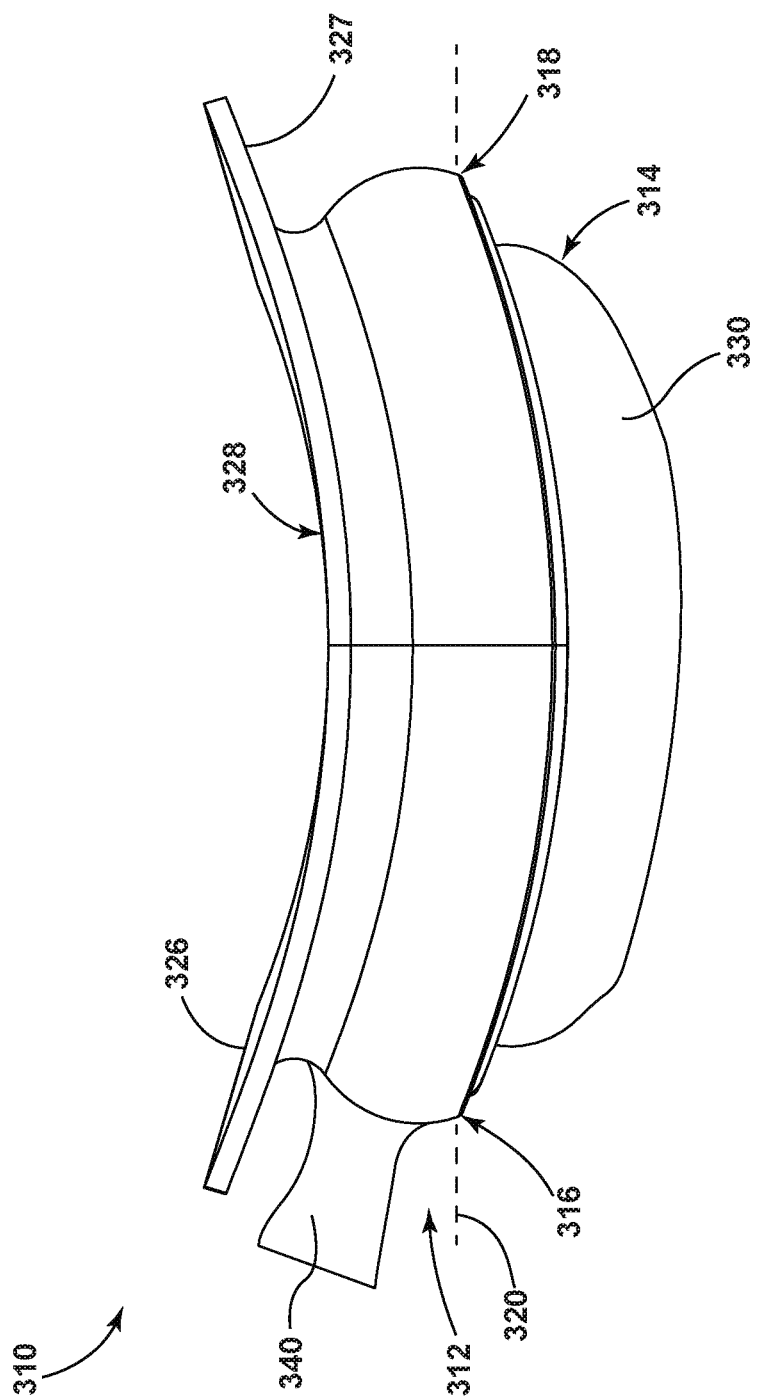
FIG. 14 is a schematic view of an external female urinary assembly according to an embodiment of the invention.

Referring now to FIG. 14, an alternative embodiment of the urinary assembly is shown and generally designated 310. This embodiment is similar in structure, function, and operation to the other embodiments described herein with several exceptions. For example, the drain 340 is formed in the sleeve 312, rather than the cup 314. Therefore, elements of the urinary assembly 310 similar to those of the urinary assembly 10 are labeled with a prefix increased by 300.

As illustrated in FIG. 14, the drain 340 is disposed in the sleeve 312 for draining urine excreted by the female user out of the urinary assembly 310. The sleeve 312 can be attached to the female user by an adhesive in the same manner as described above for the sleeve 12. The sleeve 312 and the cup 314 can be coupled together to form a liquid tight seal in the same manner as described above for the sleeve 12 and cup 14. The drain 340 can be formed in the sleeve 312 generally adjacent the posterior end 316 of the urinary assembly 310 in order to drain urine collected within the sleeve 312 and cup 314 away from the user's body.

The external female urinary assembly described herein provides several benefits and advantages. The urinary assembly is attached to the female user through an adhesive attachment to an external portion of the user's body, without inserting components into the user's urethra. Attaching the urinary assembly externally can decrease the likelihood of UTIs compared to indwelling catheters. External attachment can also be easier and/or quicker to install than indwelling catheters because sterile processes do not have to be used.

The two-part sleeve and cup configuration of the urinary assembly described herein can facilitate aligning and attaching the urinary assembly. The two-part configuration also provides the ability to inspect and clean the area adjacent the user's external urethral orifice without having to completely remove and then reattach the urinary assembly. The sleeve can be attached to the user without the cup attached, thus allowing the installer to align the sleeve around the user's urethral orifice. During use of the urinary assembly, the cup can be temporarily separated from the sleeve while the sleeve remains adhesively attached to the user. Removal of the cup allows the area around the urethral orifice to be cleaned and/or inspected and also allows the cup to be cleaned, quickly and easily. The cup can then be recoupled to the sleeve for continued use of the urinary assembly. Leaving the sleeve in place while the cup is removed minimizes the number of times that the adhesive is removed from the user's body, which can be an uncomfortable and sometimes painful process.

The adhesive can be selected to provide a liquid tight seal between the user's body and the sleeve for a predetermined period of time prior to removal. The adhesive can also be selected to facilitate retaining the urinary assembly in place on the user while also allowing the urinary assembly to be removed without excessive discomfort or damage to the user's skin. An undergarment, such as described herein, can be worn by the user to facilitate holding the urinary assembly in place against the user's and maintaining the liquid tight seal between the user's body and the sleeve.

The urinary assembly can be made from a flexible material that facilitates conforming the sleeve to the user's body to form the liquid tight seal. The urinary assembly can also have a 3-dimensional shape and contouring that is reflective of the shape and contouring of the female body around the external urethral orifice to facilitate attaching the urinary assembly to the female user. The urinary assembly can also be formed in multiple different sizes to allow for a more custom fit to each user based on body characteristics, such as height and weight. Forming the cup from a flexible material can also make wearing the urinary assembly more comfortable to wear while sitting and/or moving.

The contouring of the urinary assembly and the positioning of the urine outlet can also be configured to facilitate draining urine away from the user's body, thus minimizing the amount of time that urine is contact with the female user's skin. The urinary assembly can be adapted for use as part of a gravity-based drain system or optionally be adapted for use with a manual or powered suction system to facilitate removing excreted urine from the urinary assembly.

All patents, patent applications, and literature references cited in this specification are hereby incorporated herein by reference in their entirety. In case of conflict, the present description, including definitions, will control.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

What is claimed is:

1. An external urine collection system for urine excreted by a user through the user's external urethral orifice, the collection system comprising:
    a posterior end and an anterior end defined with respect to an anatomical orientation of the collection system when the collection system is worn by the user, with the posterior end positioned posterior of an external urethral orifice of the user and the anterior end positioned anterior of the external urethral orifice of the user;
    a longitudinal axis extending between the posterior end and the anterior end;
    a sleeve having an interface surface defining an open end, the interface surface comprising a curved surface that corresponds to a curvature of an external surface of the user surrounding the external urethral orifice of the user, the curved surface configured to be secured via an adhesive to the external surface of the user and to surround the external urethral orifice of the user, distal from the external urethral orifice, the sleeve defining a sleeve outlet, opposite the open end;
    a removable cup coupled with the sleeve at the sleeve outlet, and including a collection chamber, wherein the cup comprises:
        a wall defining the collection chamber and including an outlet through which urine in the collection chamber exits the cup, wherein the outlet is disposed between the anterior and posterior ends and the outlet is spaced from and disposed opposite to the sleeve outlet; and
        a drain fluidly connected with the outlet through which urine in collection chamber can exit the cup, the drain projecting from the wall in a direction transverse to the longitudinal axis; and
    a releasable coupling between the cup and the sleeve, the releasable coupling forming a liquid tight seal for the flow of urine through the sleeve and into the cup;
    wherein the cup can be uncoupled from the sleeve while the sleeve remains secured via the adhesive to the external surface of the user.

2. The external urine collection system of claim 1 wherein the interface surface of the sleeve includes a flange extending outward and away from the open end, wherein the flange provides a surface area sufficient to form an adhesive bond with the external surface of the user to hold the sleeve in place.

3. The external urine collection system of claim 2 wherein the flange is contoured to define the curved surface.

4. The external urine collection system of claim 1 wherein the cup comprises a cup inlet removably joined with the sleeve about the sleeve outlet.

5. The external urine collection system of claim 1:
    wherein the outlet is disposed in the wall along the longitudinal axis extending between the anterior and posterior ends.

6. The external urine collection system of claim 5 wherein the outlet is disposed closer to the posterior end than the anterior end.

7. The external urine collection system of claim 1 wherein the releasable coupling comprises:
    a male connector disposed on one of the sleeve and the cup; and
    a female connector disposed on the other of the sleeve and the cup, the male connector configured to removably couple with the female connector to form the liquid tight seal therebetween.

8. The external urine collection system of claim 7 wherein the female connector comprises an inner flange and an outer flange defining a channel therebetween, the channel adapted to receive the male connector therein to form the liquid tight seal between the sleeve and the cup.

9. The external urine collection system of claim 8 wherein the female connector is disposed on the sleeve, and the inner flange defines the sleeve outlet and forms a sleeve wall that, together with the cup, defines the collection chamber.

10. The external urine collection system of claim 8 wherein at least one of the inner flange and the outer flange is resilient, and is configured to flex toward and away from the other one of the inner flange and the outer flange.

11. The external urine collection system of claim 8 comprising:
    a rib disposed on at least one of the inner flange and the outer flange and extending into the channel and around a periphery of the channel; and
    a seal recess defined by the male connector,
    wherein the rib is adapted to engage the seal recess when the male connector is removably coupled to the female connector.

12. The external urine collection system of claim 8 wherein the male connector comprises a leg adapted to fit and be received within the channel.

13. The external urine collection system of claim 7 wherein the cup comprises:
the male connector; and
a cup inlet through which urine excreted into the sleeve passes into the cup;
wherein the cup inlet is defined by a wall that is separate from and disposed inwardly of the male connector; and
wherein the male connector extends around the wall defining the cup inlet such that the male connector can form a liquid tight seal with the female connector around a periphery of the wall defining the cup inlet.

14. The external urine collection system of claim 7 wherein;
the male connector extends around a periphery of one of the sleeve outlet and an inlet of the cup;
the female connector extends around the periphery of the other one of the sleeve outlet and an inlet of the cup; and
the releasable coupling forming the liquid tight seal for the flow of urine through the sleeve through the sleeve and into the cup around the periphery of the sleeve outlet.

15. The external urine collection system of claim 1 comprising a vent in at least one of the sleeve and the cup for venting the collection chamber.

16. The external urine collection system of claim 1 comprising:
an undergarment comprising:
a first portion configured to extend at least partially between a user's legs, the first portion including an opening configured to receive the cup; and
a second portion configured to extend around a user's torso to hold the undergarment in place,
wherein the undergarment is configured to provide at least intermittent support to at least one of the sleeve and cup to facilitate maintaining the sleeve in place adjacent the user's external urethral orifice.

17. The external urine collection system of claim 1 wherein at least one of the sleeve and the cup are made from a flexible polymeric material, and wherein the adhesive comprises at least one of a hydrogel, a silicone-based adhesive, and a polyethylene glycol (PEG) hydrogel adhesive.

18. An external urine collection system for urine excreted by a user through the user's external urethral orifice, the collection system comprising:
a posterior end and an anterior end defined with respect to an anatomical orientation of the collection system when the collection system is worn by the user, with the posterior end positioned posterior of an external urethral orifice of the user and the anterior end positioned anterior of the external urethral orifice of the user;
a longitudinal axis extending between the posterior end and the anterior end;
a sleeve having an interface surface defining an open end, the interface surface comprising a curved surface that corresponds to a curvature of an external surface of the user surrounding the external urethral orifice of the user, the sleeve defining a sleeve outlet, opposite the open end;
an adhesive configured to secure the curved surface to the external surface of the user around the external urethral orifice of the user;
a removable cup coupled with the sleeve at the sleeve outlet, and including a cup inlet and a collection chamber, wherein the cup comprises:
a wall defining the collection chamber and including an outlet through which urine in the collection chamber exits the cup, wherein the outlet is disposed between the anterior and posterior ends and the outlet is spaced from and disposed opposite to the sleeve outlet; and
a drain fluidly connected with the outlet through which urine in collection chamber can exit the cup, the drain projecting from the wall in a direction transverse to the longitudinal axis; and
a releasable coupling between the cup and the sleeve, the releasable coupling extending around a periphery of the sleeve outlet and the cup and forming a liquid tight seal for the flow of urine through the sleeve and into the collection chamber of the cup;
wherein the cup can be uncoupled and removed distally from the sleeve while the sleeve remains secured via the adhesive to the external surface of the user.

19. The external urine collection system of claim 1 comprising an adhesive on the curved surface configured to secure the sleeve to the external surface of the user around the external urethral orifice of the user, distal from the external urethral orifice;
wherein the adhesive is configured to maintain a liquid tight seal between the sleeve and the external surface of the user and to retain the sleeve in place for a minimum period of 24 hours.

20. The external urine collection system of claim 1 comprising a lateral axis extending perpendicular to the longitudinal axis, wherein the curved surface curves inwardly from the posterior end toward the lateral axis in a first direction along the longitudinal axis and inwardly the anterior end toward the lateral axis in a second, opposing direction along the longitudinal axis.

* * * * *